(12) United States Patent
Beymore et al.

(10) Patent No.: US 10,178,351 B2
(45) Date of Patent: Jan. 8, 2019

(54) MULTI-ANGULAR COLOR, OPACITY, PIGMENT CHARACTERIZATION AND TEXTURE ANALYSIS OF A PAINTED SURFACE VIA VISUAL AND/OR INSTRUMENTAL TECHNIQUES

(71) Applicant: PPG Industries Ohio, Inc., Cleveland, OH (US)

(72) Inventors: Paul M. Beymore, Vermillion, OH (US); James Pereksta, Rocky River, OH (US)

(73) Assignee: PPG Industries Ohio, Inc., Cleveland, OH (US)

( * ) Notice: Subject to any disclaimer, the term of this patent is extended or adjusted under 35 U.S.C. 154(b) by 606 days.

(21) Appl. No.: 13/832,088

(22) Filed: Mar. 15, 2013

(65) Prior Publication Data

US 2014/0078293 A1 Mar. 20, 2014

Related U.S. Application Data

(60) Provisional application No. 61/702,959, filed on Sep. 19, 2012.

(51) Int. Cl.
H04N 7/18 (2006.01)
G01J 3/50 (2006.01)
G01N 21/84 (2006.01)

(52) U.S. Cl.
CPC ............... *H04N 7/18* (2013.01); *G01J 3/504* (2013.01); *G01N 21/8422* (2013.01); *G01N 2021/8427* (2013.01); *G01N 2021/8433* (2013.01)

(58) Field of Classification Search
CPC . G06Q 10/06; H04N 7/18; G01J 3/463; G01J 3/00; B05C 21/00; G06F 7/06;
(Continued)

(56) References Cited

U.S. PATENT DOCUMENTS 5,231,472 A * 7/1993 Marcus .............. G01N 21/4738
356/402
5,929,998 A 7/1999 Kettler et al.
(Continued)

FOREIGN PATENT DOCUMENTS

CN 101023332 8/2007
CN 101730835 6/2010
(Continued)

OTHER PUBLICATIONS

X-Rite Inc., X-Rite MA98 Measured Material, Portable Multi-Angle Spectrophotometer, copyright date of 2010.*

*Primary Examiner* — Maryam A Nasri
(74) *Attorney, Agent, or Firm* — Workman Nydegger

(57) ABSTRACT

A computer implemented method. The method includes performing at least one of a visual evaluation and an instrument measurement of a target coating on a target sample to generate colorimetric information, and identifying, using a processor, a bulk toner that is present in the target coating by determining a color and a color intensity at different viewing angles relative to the target sample. The method also includes identifying, using the processor, at least one specific toner that is present in the target coating by detecting a presence and an orientation of colored and/or non-colored pigmentation effects that are present in the target coating, and outputting, using the processor, a formulation of the target coating that includes at least the at least one specific toner.

16 Claims, 6 Drawing Sheets

(58) Field of Classification Search
CPC ......... G06F 17/30; B32B 43/00; G01N 21/00;
G01N 2021/00
See application file for complete search history.

(56) References Cited

U.S. PATENT DOCUMENTS

| | | |
|---|---|---|
| 7,804,597 B2 | 9/2010 | De Haas et al. |
| 8,629,882 B2 | 1/2014 | Henry |
| 2005/0128484 A1 | 6/2005 | Rodrigues et al. |
| 2006/0181707 A1* | 8/2006 | Gibson ............... B01F 13/1055 356/402 |
| 2007/0250273 A1 | 10/2007 | De Haas et al. |
| 2009/0274827 A1 | 11/2009 | Anderson et al. |
| 2009/0295823 A1 | 12/2009 | Henry |

FOREIGN PATENT DOCUMENTS

| | | |
|---|---|---|
| CN | 102449644 | 5/2012 |
| CN | 102549545 | 7/2012 |
| CN | 102667444 | 9/2012 |
| EP | 0828144 A2 | 3/1998 |
| JP | 58076741 | 3/2005 |
| JP | 2007505202 | 3/2007 |
| JP | 2012173272 | 9/2012 |
| NZ | 589596 A | 7/2012 |
| WO | 20040101689 | 11/2004 |
| WO | WO 2006/030028 A1 | 3/2006 |
| WO | 2008/103405 A1 | 8/2008 |

* cited by examiner

MULTI-ANGULAR COLOR, OPACITY, PIGMENT CHARACTERIZATION AND TEXTURE ANALYSIS OF A PAINTED SURFACE VIA VISUAL AND/OR INSTRUMENTAL TECHNIQUES

CROSS REFERENCE TO RELATED APPLICATION

The present application claims priority to U.S. Provisional Patent Application No. 61/702,959, filed Sep. 19, 2012.

FIELD OF THE INVENTION

In various embodiments, the present invention generally relates to a method and apparatus for evaluating colorimetric and physical property attributes of cured complex coating (e.g., paint) mixtures.

BACKGROUND OF THE INVENTION

Various techniques (e.g., SAE® J361) that are used to evaluate the properties of complex coating (e.g., paint) mixtures typically include a variety of in-plane viewing conditions that are often combined with microscopic evaluation of a sample. However, such techniques generally do not adequately address new effect pigmentations in complex paint mixtures. Further, they are largely focused on textiles and use obscurely identified out-of-plane viewing angles that require at least two light sources for viewing effect pigmentations properly. Other techniques involve using a spectrophotometer (i.e., in-plane multi-angle devices for effect samples and spherical devices for straight shade samples) that are generally effective for analyzing pigmentations. However, such techniques are generally not able to adequately characterize new pigments due to the unique properties of, for example, Colorstream® pigments that include pearls, colored aluminums, etc. because it is very difficult to view the coarseness of colored aluminums. Thus, a microscope is required to adequately determine special effect pigments, thus adding time and complexity while not satisfactorily addressing application issues which modify the characteristics of the sample and the effect of the special pigments.

Laboratory gonio spectrophotometers are not able to be effectively used in either the field or the laboratory due to constraints such as size, cost, performance, and measurement time. Portable gonio spectrophotometer devices include CCD cameras such as the Byk Mac® device from Byk-Gardner, or under-sampled bidirectional reflectance devices such as the MA98 device from X-Rite, Inc. While these devices demonstrate an improvement over the existing portable equipment available to provide coarseness, sparkle, and additional previously unavailable information, the devices do not provide simple data streams or conclusive texture and opacity information. CCD cameras generating sparkle and graininess values are inaccurate and provide generic values so that pigment identification/characterization and textural information is inaccurate even when used in conjunction with texture scales and spectral data. Under-sampled bidirectional reflectance devices use a complex amount of datastreams and rely on overcomplicated scattering properties of pigments to either "fingerprint" pigments or sample defects.

None of the aforementioned devices provide adequate information for identification of and property analysis of effect pigmentations, such as colored aluminums because, in part, the devices provide inadequate results due to the underlying assumption that coarseness is not an attributable characteristic and only sparkle is an appropriate measure. However, different aluminums (colored or otherwise) clearly demonstrate coarseness qualities in collimated light and thus there may be confusion with regard to visually different aluminum pigments that appear identical to the devices, and the suggested usage of those devices. Furthermore, the devices typically require traditional, advanced, or complex proprietary colorimetric functions that use weighting functions to produce moderate results.

Further strategies have been developed using painted or virtual samples that represent various textures and that are compared to unknown samples. These techniques require substantial user intervention and are subjective in nature and thus may yield inconsistent results depending on the skill of the user.

Thus, a need exists for a simplified approach that uses limited multiangle, multiplanar spectral and/or visual data with or without a color camera that can produce improved and simplified results for pigment characterization and sample properties so that application (opacity) issues and texture issues can be quickly and clearly identified to allow for faster and better color matching.

SUMMARY OF THE INVENTION

In various embodiments the present invention is directed a computer implemented method. The method includes performing at least one of a visual evaluation and an instrument measurement of a target coating on a target sample to generate colorimetric information, and identifying, using a processor, a bulk toner that is present in the target coating by determining a color and a color intensity at different viewing angles relative to the target sample. The method also includes identifying, using the processor, at least one specific toner that is present in the target coating by detecting a presence and an orientation of colored and/or non-colored pigmentation effects that are present in the target coating, and outputting, using the processor, a formulation of the target coating that includes at least the at least one specific toner.

In various embodiments the present invention is directed to a system. The system includes a user interface and a processor in communication with the user interface and programmed to receive data from at least one of a visual evaluation and an instrument measurement of a target coating on a target sample to generate colorimetric information. The processor is also programmed to identify a bulk toner that is present in the target coating by determining a color and a color intensity at different viewing angles relative to the target sample and identify at least one specific toner that is present in the target coating by detecting a presence and an orientation of colored and/or non-colored pigmentation effects that are present in the target coating. The processor is further programmed to output a formulation of the target coating that includes at least the at least one specific toner.

In various embodiments the present invention is directed to an apparatus. The apparatus includes means for receiving data from at least one of a visual evaluation and an instrument measurement of a target coating on a target sample to generate colorimetric information, and means for identifying a bulk toner that is present in the target coating by determining a color and a color intensity at different viewing angles relative to the target sample. The apparatus also includes means for identifying at least one specific toner that is present in the target coating by detecting a presence and an orientation of colored and/or non-colored pigmentation effects that are present in the target coating, and means for outputting a formulation of the target coating that includes at least the at least one specific toner.

In various embodiments, the present invention is directed to a non-transitory computer readable medium including software for causing a processor to:

receive data from at least one of a visual evaluation and an instrument measurement of a target coating on a target sample to generate colorimetric information;

identify a bulk toner that is present in the target coating by determining a color and a color intensity at different viewing angles relative to the target sample;

identify at least one specific toner that is present in the target coating by detecting a presence and an orientation of colored and/or non-colored pigmentation effects that are present in the target coating; and output a formulation of the target coating that includes at least the at least one specific toner.

DETAILED DESCRIPTION OF THE INVENTION

In various aspects, embodiments of the invention include a spectrophotometer and a method that may be used to obtain target spectral and visual information for a target sample, characterize toners to identify a plurality of bulk toner types (i.e., a grouping of toner types such as pearls, aluminums, colored aluminums, etc. that have similar physical layering and properties) that can be used to produce a coating having a color, texture i.e., the non-uniform topographical appearance), and opacity that is similar to the target sample, and determine if the coating composition meets user specified acceptance criteria.

Various embodiments of the invention include the identification of "best fit" individual/specific toners that can be used to produce a paint having color, texture, opacity, and effect properties nearly or substantially identical to those in the target sample. Embodiments may also identify inadequacies of toners such that specific missing toners are identified which are necessary to make a paint formulation match that meets user specified acceptance criteria.

Various embodiments of the invention include an apparatus that has a device for capturing information for a target sample and a processor for identifying bulk toner types and specific toners that can be used to produce a paint having a color that is similar to the target sample. The processor also determines if the modified paint composition or formula meets user specified acceptance criteria. An output device may be used for conveying the paint formula information to a user to visualize how a coating will appear on one or more surfaces. In various embodiments, the invention provides a method and apparatus for a user to visualize how an interior or exterior surface of an object such as a portion of a structure (e.g., a wall), an automobile, etc., will appear after the surface has been coated with, for example, one or more paint colors.

While the description herein generally refers to paint, it should be understood that the devices, systems and methods apply to other types of coatings, including stain and industrial coatings. The described embodiments of the invention should not be considered as limiting. A method consistent with the present invention may be practiced in a variety of fields such as the matching and/or coordination of apparel and fashion products.

Embodiments of the invention may be used with or incorporated in a computer system that may be a stand alone unit or include one or more remote terminals or devices in communication with a central computer via a network such as, for example, the Internet or an intranet. As such, the computer or "processor" and related components described herein may be a portion of a local computer system or a remote computer or an on-line system or combinations thereof. The database and software described herein may be stored in computer internal memory or in a non-transitory computer readable medium.

Figure 1:
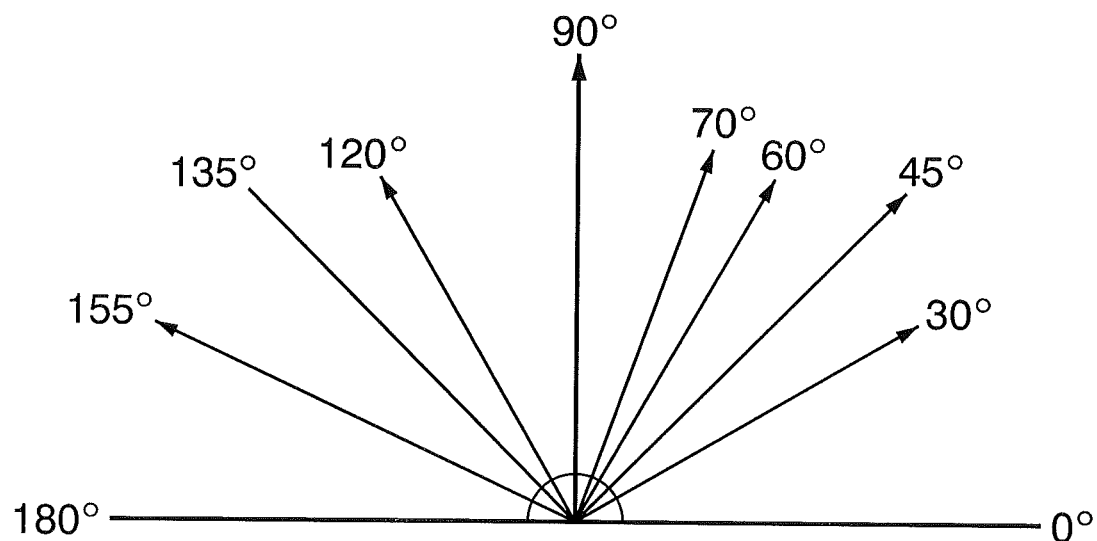
FIG. 1 illustrates angles labeled according to standard mathematical terminology.
Figure 2:
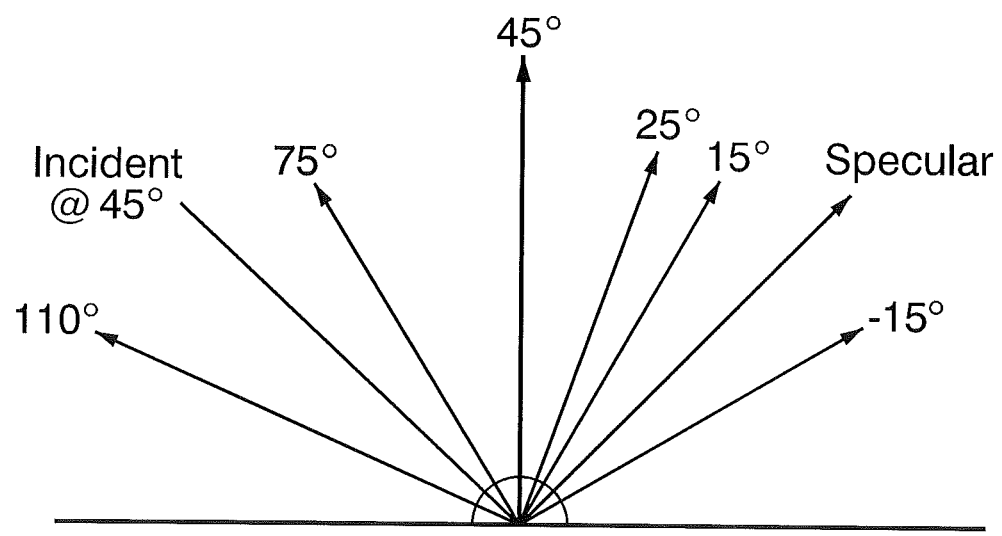
FIG. 2 illustrates the angles of FIG. 1 labeled according to standard multi-angle spectrophotometer terminology.

Traditional spectrophotometers and visual viewing conditions consider the angles and light sources illustrated in FIGS. 1 and 2. FIGS. 1 and 2 illustrate the same angles, but FIG. 2 uses generally accepted terminology to describe the angles in relation to the specular angle (i.e., the angle of specular reflection of the incident light source) when discussing multi-angle spectrophotometers. However, for clarity the angle labeling system illustrated in FIG. 1 is used herein. In various embodiments, traditional light sources may be used that employ diffuse or collimated color corrected light.

In various embodiments, in order to properly identify the type of toners used in the coating that is applied to the surface of an unknown or target sample, observations are taken at appropriate angles and the observed data are compared to existing known toners in a database. The database may include properties of existing toners with which the comparison is made.

Figure 3:
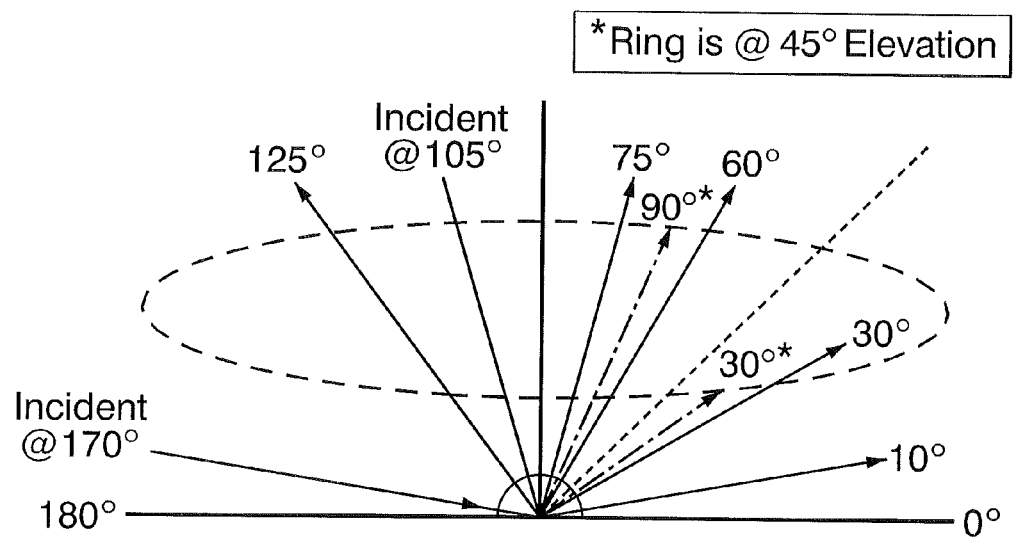
FIG. 3 illustrates specific angles at which visual and/or spectral information may be captured to characterize toners.
Figure 4:
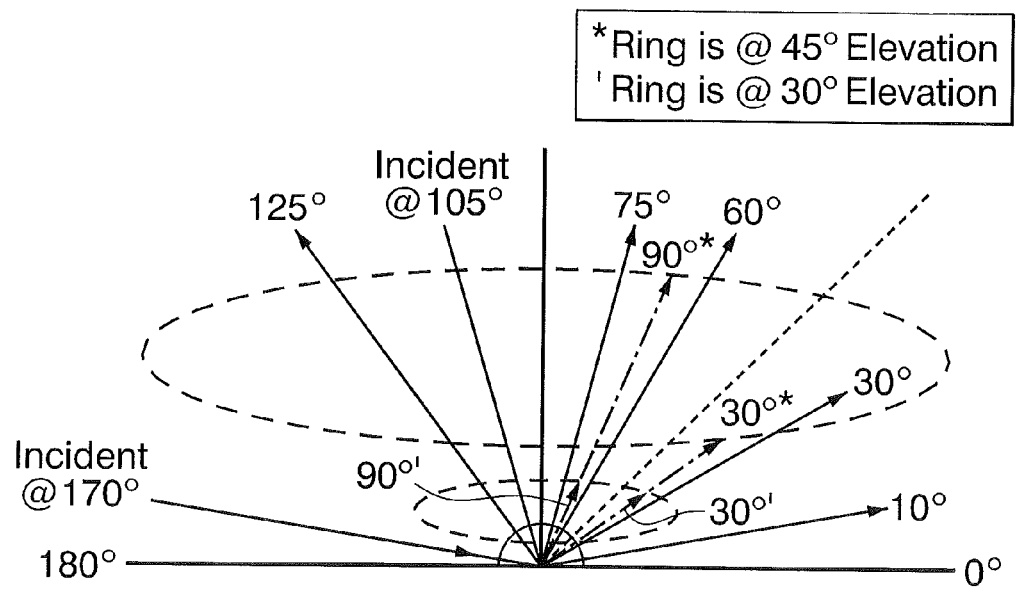
FIG. 4 illustrates a maximum number of angles at which visual and/or spectral information may be captured to characterize toners.
Figure 5:
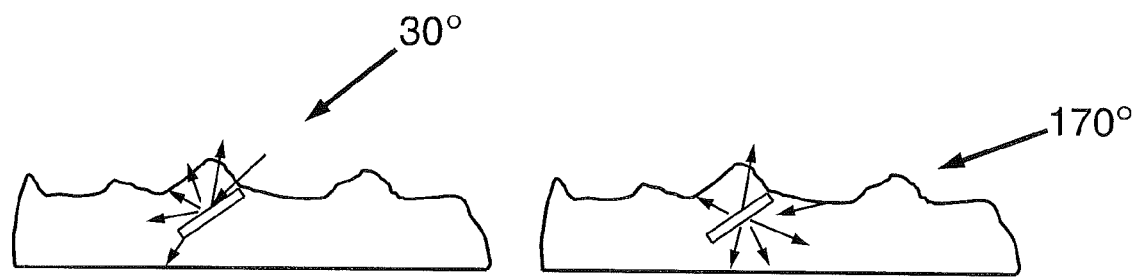
FIG. 5 illustrates various angles with respect to a painted sample and light interaction with a typical transparent or semi-transparent effect flake.

In various embodiments, two incident light sources may be used to characterize toners. As illustrated in FIG. 3 the incident light at 105° acts as a bright spotlight on the sample and allows an observer (which may also be a camera) and/or a spectrophotometer to capture reflectance details regarding the target's color and flake (i.e., effect) orientation. The incident light may be brighter and more direct than what would be present when an individual observes the painted surface in a natural light environment. By using the incident light, the properties of the coating are thus exaggerated, making it easier to quantify the minute characteristics of the particles within the coating. A second incident light at 170° that is representative of an individual looking along the length of a coated surface (e.g., a vehicle) allows for better evaluation of the color and toner characteristics. As illustrated in FIG. 5, the incident light that is nearly parallel to the target interacts substantially different with translucent toners such as micas, pearls, xirallics, glass flakes, etc. than light sources at angles more normal to the target. At the 10° (where 170° is the equal, but opposite) angle of illumination the coating layer is able to be "seen" from the underside, which results in much more transmitted light returned to the viewer than reflected light. This provides opacity information, unique color data, and identifies flake orientation for characterization of toners in a simple or complex coating mixture. Furthermore, light reflected at this angle provides a greater span of reflected information and colors which may be critical for identification of certain effect pigments with significant color variation over the travel.

Figure 6:
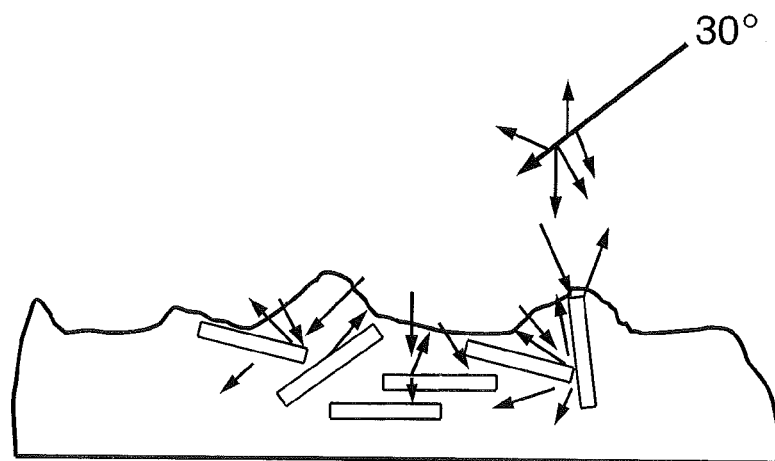
FIG. 6 illustrates how diffuse light sources provide unfocused light to provide randomized information.

Due to the complex interaction of translucent toners with light, direct, collimated light sources may be used to ensure consistency and repeatability when reviewing a target sample. FIG. 6 illustrates how diffuse light sources provide an unfocused light and allow for significant "random" interactions with effects such as metallic flakes, resulting in inadequately repeatable measurements by providing randomized information to the viewer at all angles. Stray light from a diffuse source is able to strike pigment effects in an inconsistent variety of locations at a variety of angles, resulting in non-reproducible reflections, thus providing information to the sensors in a spectrophotometer or to the receptors in an observer's eyes. The unique characteristics of the effect pigments are diffused, thus eliminating the possibility of identification of the effect pigment. Collimated light has no stray light emanating from the source beam, so it returns the same reflections every time a target surface is viewed. This rationale may be used to populate pigment data in a database. It may also be desirable to use similar lights in similar orientations when developing a database to which to compare the target information.

Figure 7:
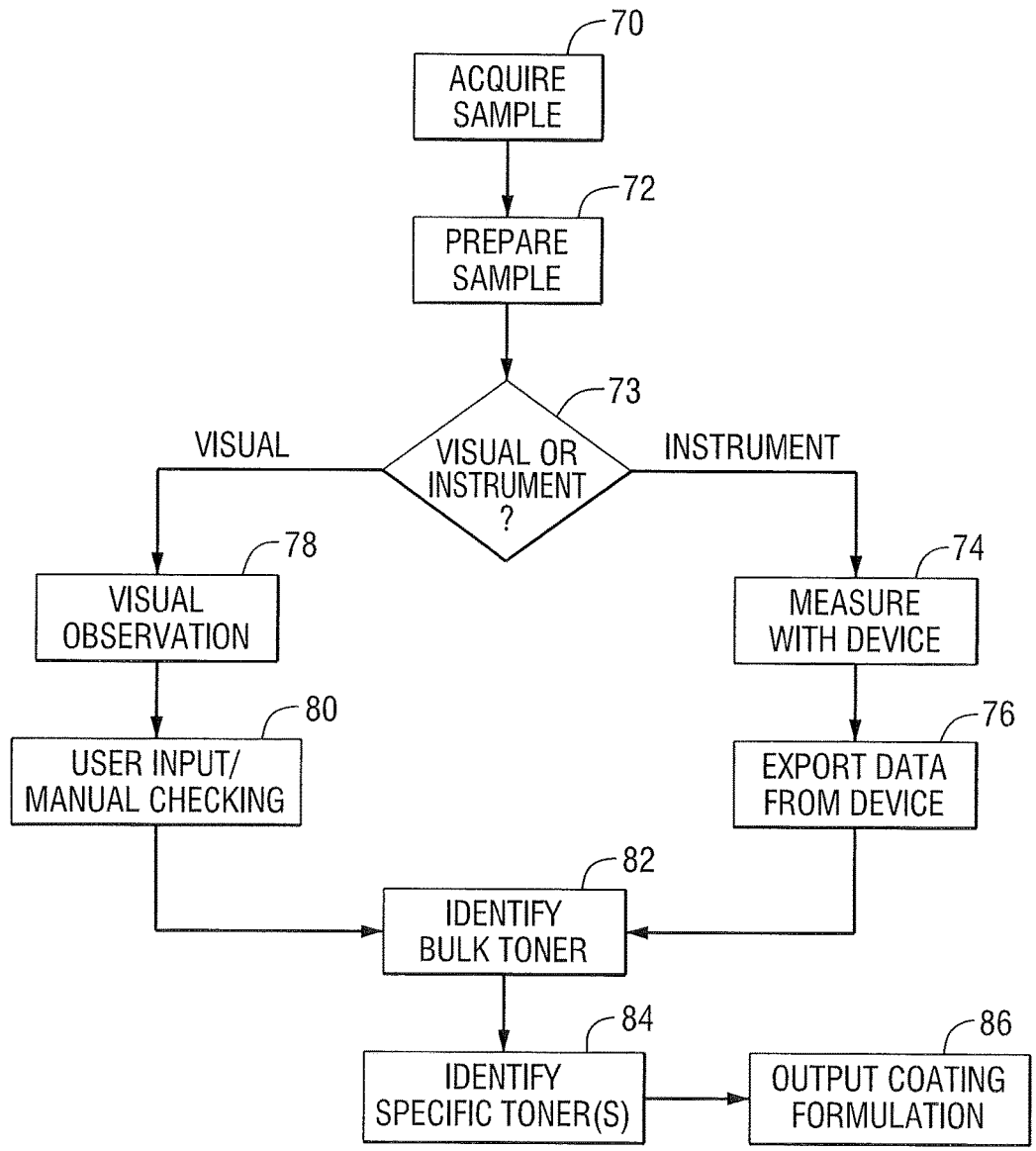
FIG. 7 illustrates a flowchart of an embodiment of a process for identifying toners used to match a target sample coating.

As illustrated in FIG. 7, embodiments of the present invention are directed to a method of analyzing a target surface to determine the composition of the coating on a target surface. At step 70, the target sample having the target surface is acquired and is prepared for analysis at step 72. At step 73, it is determined, based on user input, whether a visual observation or instrument measurement is to be conducted. If an instrument measurement is to be conducted, at step 74 color cameras included within a device such as a spectrophotometer acquire Red, Green and Blue (RGB) information. At the same time a spectrophotometer could supply colorimetric values such as L*, a*, b*, C, and h. At step 76 the information is exported from the device to a user device. The information can be used to directly compare information viewed at different angles. A tolerance difference in the RGB or colorimetric information of 0.5 to 1.0 during a comparison for any of the three values is generally indicative of a different color or different color intensity.

Visual evaluation of a target coating composition is performed at step 78, and may require an observer to make a decision at step 80 as to which color is most prominent at a given angle. In various embodiments, this may be resolved based on the most chromatic hue observed at the given angle. For example, at a particular viewing angle a target coating may appear dull green, but may contain substantial flecks of violet. Because violet is the most prominent color at the given angle, violet is designated as the color of the angle and used for the purposes of comparison. The color may also be interpreted as having a particular intensity which would be designated as the intensity of the color at the given angle. The intensity may be measured on, for example, a 3 to 5 point scale that ranges from less intense to moderately intense to highly intense.

Spectral data provided by a spectrophotometer requires data manipulation at step 82, but can eliminate the subjectivity of visual observation or the restrictiveness of using a camera. In various embodiments, the comparison of spectral data between angles involves one of two procedures. The first procedure is to evaluate the peak of greatest reflectance and compare that reflectance value at a given wavelength to those in a database in which colors have been assigned to a range of wavelengths. For example, a spectral reflectance may peak at or around 550 nm for a sample. When compared to wavelength values for particular colors in a database, the color may be matched with "Green," which has a range of 525-575 nm stored in the database (i.e., "Green" would be the most prominent color at the evaluated angle). Following the visual process the "color" at the evaluated angle is compared to a color observed at another angle. The difference between the magnitudes of the spectral reflectance at the peak of each angle signifies the intensity difference between the angles under consideration. Following the procedure for comparing spectral data between angles involves the generation of an augmented similarity, or reflective, index (SI). The spectral curve at the angles under consideration is normalized and the division of the absolute values of the differences between the normalized values at each wavelength summed by 2 times the number of wavelengths considered yields the augmented SI. Exceeding a value range of 0.2-0.4 may indicate that the colors under consideration are different. A value of 0.2 may be desirable for tighter control given a large overall starting comparison pool or in a white/silver/black color whereas a value of 0.4 may be desirable for a smaller overall starting comparison pool or larger inclusion of similar colors from the pool. In various embodiments, the process for considering intensity is substantially the same as the process described herein in connection with the first procedure for comparing spectral data between angles.

Equation 1: Similarity Index for a Given Single Angle $$SI = \frac{\sum_{0}^{n} |R_s - R_d|}{2n_\lambda}$$

Where:
n=total number of wavelengths
R=normalized reflectance value
s=sample
d=database Bulk characterization of toners is performed because the correct interpretation of a toner type will lead to the correct texture of the final coating. For example, pearls generally have identical coarseness values, but specific pearls result in unique colored sparkle characteristics. Furthermore, aluminums have similar color values, but may have unique overall texture properties. Therefore, further characterization of the toner present in the coating is performed at step 84, and once a suitable toner is identified as an option for use via angular comparisons, the texture of the coating will thus be properly identified (i.e., the proper texture will be present with a reasonable toner selection). It is not necessary to identify the exact toner used in the coating, but rather a suitable selection of toners will address color and texture issues. At step 86, the coating formulation that matches (or substantially matches in an acceptable manner) the target coating is output.

In order to determine the bulk toner characteristics of a target coating at step 82, different viewing angles may be assessed and compared to one another using a light source, for example at 170°. For example, the 30° and 60° in-plane angles may be assessed for color (red, green, etc.) via a visual evaluation, a color camera, or interpretation of the spectral curve as discussed hereinabove. The 90° and 30° out-of-plane angles at a 45° elevation may then also be assessed for color in the same manner. If the colors are not within a particular tolerance of one another then there is a pearl effect (e.g., mica, xirallic, colorstream, harlequin, etc.) in the target coating. Depending on the color and color intensity difference there may also be a colored aluminum flake present (color intensity will be much higher in the in-plane angles and the color of the aluminum will be much more prevalent there also). Further consideration may also be given to the travel of the target over the range of in-plane angles. If the color intensity changes between the 125°, 60°, and 30° angles then the target likely contains an aluminum flake. If the color or color intensity does not change across any of the angles, then the target coating does not contain effect toners and only has straight shade toners present.

As described hereinabove, once the toner type has been generally determined at step 82, toners may be more specifically characterized and compared to a database for selection from one or more toners at step 84. The target at each angle may be evaluated and compared to data in a database that contains angular information for each toner. The angular information may include spectral data, visual color assignments, application implications of each toner, generic application information that can be applied to individual toners, alignment/opacity information based on the comparison of the out-of-plane angles which are within opposing planes compared to the in-plane angles, and any other appropriate data.

A colored aluminum is determined to be within a target coating based on a comparison with the characteristics of colored aluminum at specific angles. A colored aluminum is largely not visible at most angles disclosed when a 170° light source is used and colored aluminum is not visible in the 90° out of plane angle. Thus, nearly all color contributed to the target by the colored aluminum is not present in the out of plane 90° angle with a 170° light source. A comparison of the colors from the in plane angles using a 105° light source to the colors (or lack thereof) from the 90° out of plane angle using a 170° light source may allow for a definite or near definite determination that a colored aluminum is present. In order to determine if the specific colored aluminum is present, the out of plane 30° angle may be evaluated with a 105° light source. The color present at such an angle may be compared to data in the database for confirmation of the more specific type of colored aluminum present (e.g., gold, red, orange, etc.). Further confirmation can be gained via a comparison of the data at other angles using a 105° light source to data in the database. However, the texture of a colored aluminum is most clearly apparent at a 30° out of plane angle using a 105° light source. Thus, the position of a spectral receptor, a visual evaluation, and/or a colored camera may be used at such an angle with such a light source.

A pearl effect present in a complex mixture may be more specifically defined by comparing the out of plane 90° angle using a 170° light source. Most effect pigmentations become substantially less color intense at such an angle with such a light source. This is illustrated in FIG. 5. Pearl effects, however, are the exception because when a pearl effect is viewed at the out of plane 90° angle using a 170° light source it becomes noticeably more color intense. The color determined to be most prominent at such an angle with such a light source may be compared to data in a database to determine the specific pearl effects that most closely exhibit the same behavior and color as observed. The characteristic colors of the target at other angles may also be compared and evaluated to ensure the correct pearl effect has been selected by considering the out of plane to in plane travel characteristic data of the pearl effect in the database as compared to the target, with, in one embodiment, the primary angle of concern being a 90° angle using a 170° light source. Color intensity of the pearl effect at such an angle with such a light source may be further compared to data in the database to determine the presence of a flattening agent and/or misalignment of the particles in the target coating. Once a pearl effect has been identified as present within the target coating, a further analysis/comparison may be made with more comprehensive data in the database that include the exact spectral curve information for each of the toners present in the database. A comparison of the spectral curves of the target to the proposed toners from the database may further identify the presence of a standard mica or xirallic (or Colorstream® xirallic) effect using the similarity index discussed hereinabove.

Micronized white can be identified by evaluating the travel of the target sample using in plane angles and a 105° or 170° light source. The angles nearest the light source may not be impacted by micronized white, but the angles further from the light source may exhibit a white/light blue hue.

Aluminum flake may be more specifically identified by comparing the characteristics of the target coating to data in the database using the process that is used for colored aluminums, as described hereinabove, with additional considerations. As discussed hereinabove, the presence of aluminum may be evaluated by determining the travel of the target coating along with the overall color of the target coating. If the overall color of the target coating appears grey or white, but substantial changes in intensity are present between angles, then there is most likely aluminum present (this may be less obvious if a white or silver pearl effect has already been characterized). The aluminum flake will exhibit a silver appearance without additional toners present. The characteristics of the target coating at a 30° out of plane angle using a 105° light source may be compared to the color intensity data for aluminum effects in the database. Because texture for aluminums is most apparent at such an angle and with such a light source, the intensity of the color at the angle may be compared to data in the database to select the proper aluminum flake by ignoring the color information of the target coating at the angle. Aluminum flakes (including colored aluminum pigments) are generally susceptible to spray variation and in various embodiments are compared against databases which contain comparative out of plane information from the 90° and 30° angles that is stored in a database. For example, the database in various embodiments contains 170° and 105° information on aluminums that have been sprayed in various alignment conditions (particularly with wet, dry, and/or electrostatic applications). Similarity comparisons at these angles determines the need for flake alignment adjusting ingredients—flop adjusters (i.e., if the aluminum response will look similar a particular application type indicating if flop adjustment pigments are necessary to add to the mixture). Additional evaluations may be performed to determine the presence of aluminum in a target sample, and the specific type of aluminum may be identified by using observations at the specular angles (a 75° angle for a 105° light source and a 10° angle for a 170° light source). Although embodiments of the present invention are described herein as contemplating light sources and observations being taken at specific angles, it should be understood that such angles are not limiting, and include ranges or less specific angles.

In various embodiments, remaining toners, for example solids, may initially be identified by considering data relating to the 90° and 30° out of plane angles with a 170° light source. Without the presence of pearl effects in the target, a 90° angle may be used to determine the remaining solid toners in the target coating. A data comparison with the most similar solid colored toners (SI comparison) or a Kubelka-Munk matching tool may be used with the spectral curve of the target coating at such an angle to provide a selection of solid toners. If a colored aluminum or effect is not present then the solid toners may be selected by comparing data at the in-plane angles to data in the database using either or both of the light sources. If a pearl effect and/or a colored aluminum is/are present then the toners most similar to the colors of the in-plane angles and the 30° out of plane angle may be selected from the database.

Via the utilization of a spectrophotometer, the process may also be used iteratively to optimize the identification process. Reflectance data from a sample made using the toners selected from the process may be subtracted from reflectance data of an unknown sample. This results in a new, "darker," reflectance curve which may then be reiterated through the process for additional toner identification. The toners selected through the latest iteration can be added to the toners from the prior iteration(s).

Figure 8:
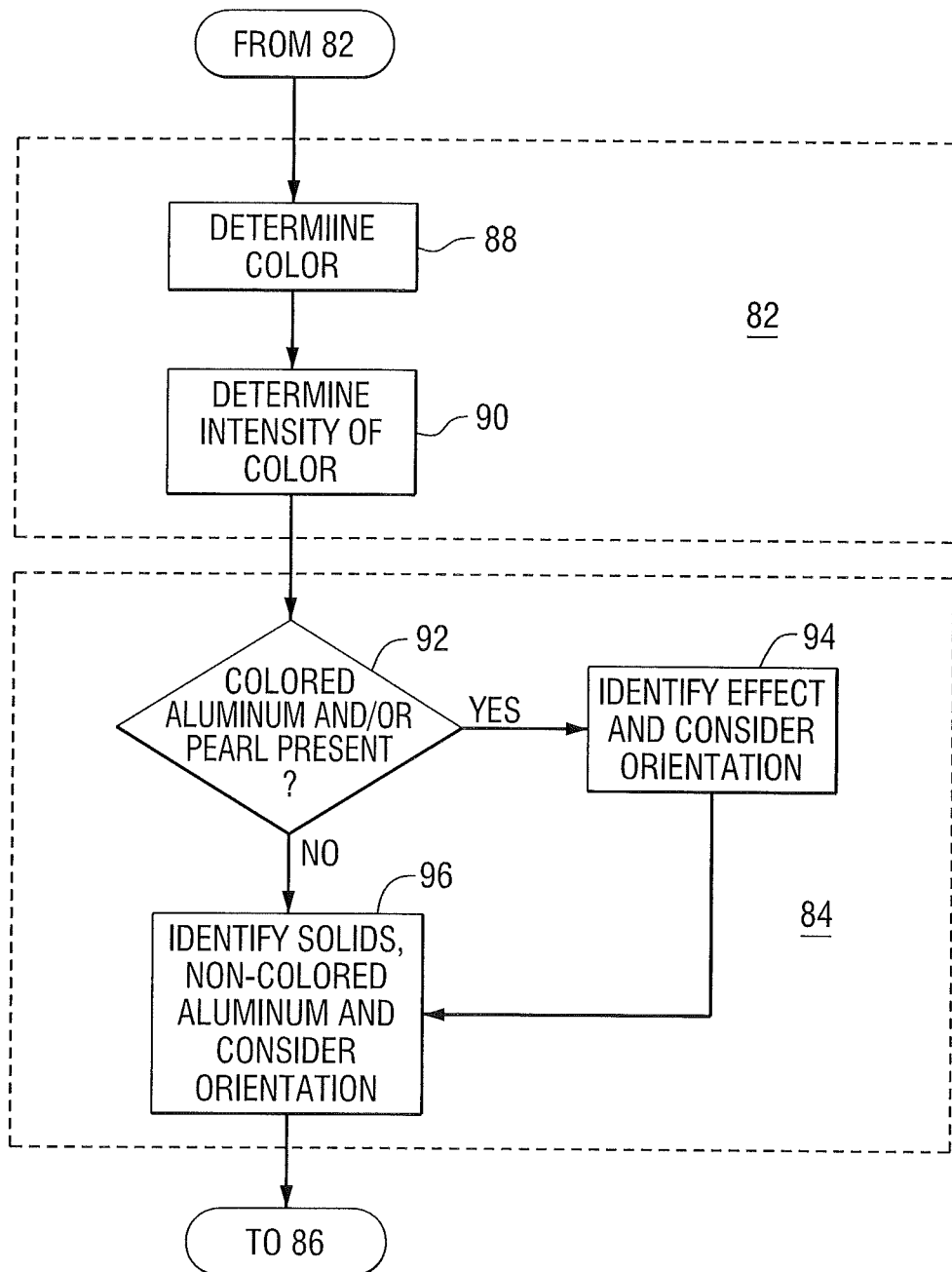
FIG. 8 illustrates a flowchart of an embodiment of a process for identifying toners used to match a target sample coating.

FIG. 8 illustrates a flowchart of an embodiment of a process for identifying toners used to match a target sample coating. At steps 88 and 90, the bulk toner is identified by determining the color at all the observed angles (step 88) and determining the intensity at all the observed angles (step 90) and described hereinabove with step 82 of FIG. 7. At step 92, it is determined whether colored aluminum and/or pearl effects are present in the target sample and, if so, at step 94 the effect (e.g., mica, xirallic, colored aluminum, glass, etc.) is identified and the effect orientation is considered as described hereinabove. At step 96, non-colored aluminum and solid effects are identified and the effect orientation is considered as described hereinabove.

Figure 9:
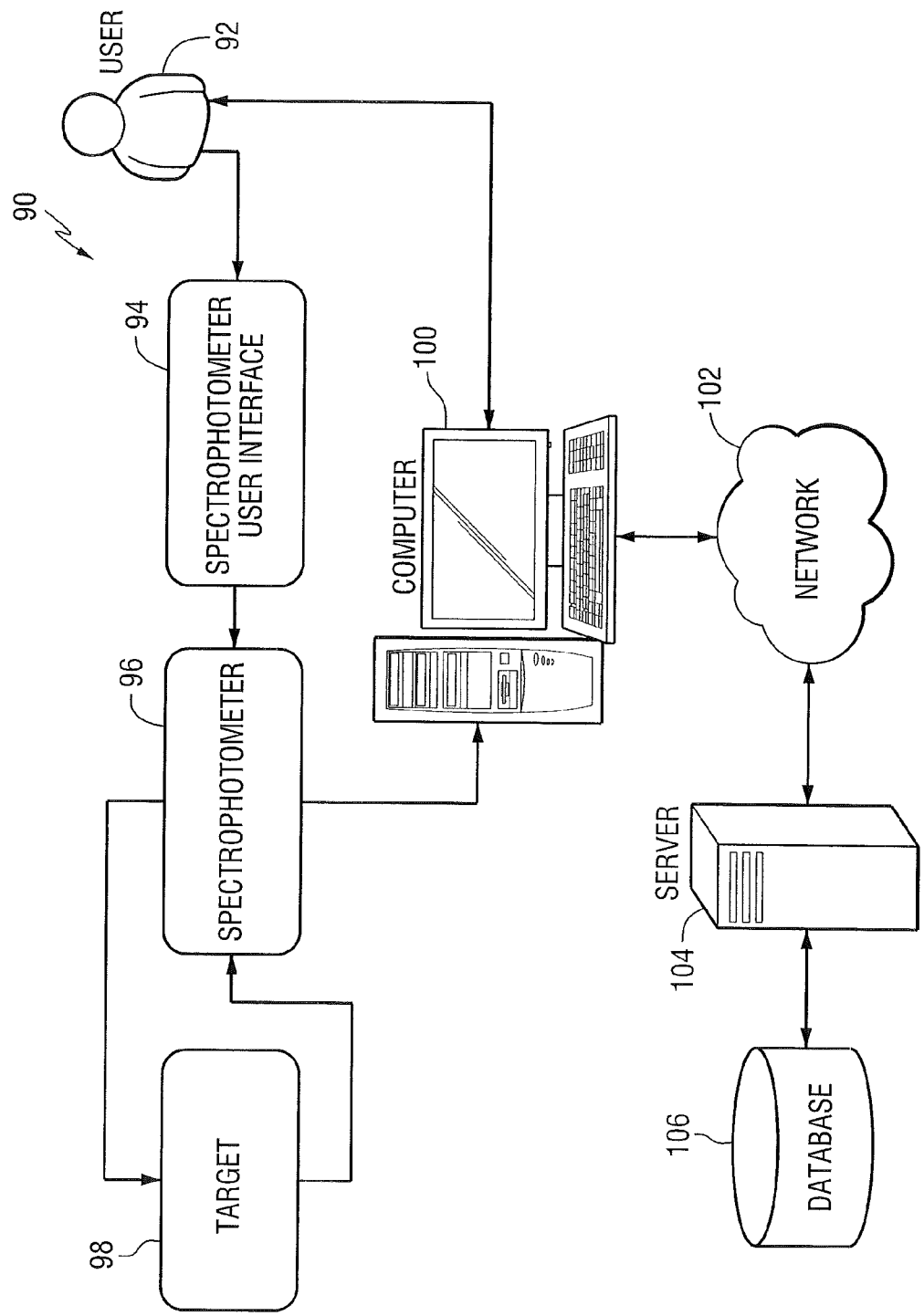
FIG. 9 illustrates an embodiment of a system which may be used to identify toners used to match a target sample coating.

FIG. 9 illustrates an embodiment of a system 90 which may be used to identify toners used to match a target sample coating. A user 92 may utilize a user interface 94, such as a graphical user interface, to operate a spectrophotometer 96 to measure the properties of a target sample 98. The data from the spectrophotometer 96 may be transferred to a computer 100, such as a personal computer, a mobile device, or any type of processor. The computer 100 may in communication, via a network 102, with a server 104. The network 102 may be any type of network, such as the Internet, a local area network, an intranet, or a wireless network. The server 104 is in communication with a database 106 that may store the data and information that is used by the methods of embodiments of the present invention for comparison purposes. Various steps of the methods of embodiments of the present invention may be performed by the computer 100 and/or the server 106.

In another aspect, the invention can be implemented as a non-transitory computer readable medium containing software for causing a computer or computer system to perform the method described above. The software can include various modules that are used to enable a processor and a user interface to perform the methods described herein.

It will be readily appreciated by those skilled in the art that modifications may be made to the invention without departing from the concepts disclosed in the forgoing description. Such modifications are to be considered as included within the following claims unless the claims, by their language, expressly state otherwise. Accordingly, the particular embodiments described in detail herein are illustrative only and are not limiting to the scope of the invention which is to be given the full breadth of the appended claims and any and all equivalents thereof.

What is claimed is:

1. A computer implemented method for evaluating colorimetric attributes of cured complex coating mixtures, the method comprising:
   performing a spectrophotometer measurement of a target coating on a target sample to generate colorimetric information;
   identifying, using a processor, a bulk toner that is present in the target coating;
   identifying, using the processor, at least one specific toner that is present in the target coating, wherein identifying the at least one specific toner comprises:
      detecting a presence and an orientation of colored and/or non-colored pigmentation effects that are present in the target coating,
      receiving an in-plane spectrophotometer measurement of one or more first colors of the target coating at a single in-plane angle,
      receiving an out-of-plane spectrophotometer measurement of one or more second colors of the target coating at a single out-of-plane angle, wherein the in-plane spectrophotometer measurement comprises different information than the out-of-plane spectrophotometer measurement,
      comparing data from the in-plane spectrophotometer measurement and data from the out-of-plane spectrophotometer measurement to data within a database that comprises information for each specific toner,
      identify that the one or more first colors, which are measured from the single in-plane angle, are not within a particular tolerance of the one or more second colors, which are measured from the single out-of-plane angle, and
      based upon the difference between the one or more first colors, which are measured from the single in-plane angle, and the one or more second colors, which are measured from the single out-of-plane angle, determine that aluminum flake bulk toners or pearl bulk toners are present in the target coating based on a comparison of the single in-plane angle and single out-plane angle at specific angles; and
   outputting, using the processor, a formulation of the target coating that includes at least the at least one specific toner.

2. The method of claim 1, wherein
the in-plane angle comprises a 30° in-plane angle and the out-of-plane angle comprises a 90° out-of-plane angle.

3. The method of claim 1, wherein when identifying an aluminum flake bulk toner, the specific angles comprise an out-of-plane angle of 30° and a light-source angle of 105°.

4. The method of claim 1, wherein when identifying a pearl bulk toner, the specific angles comprise an out-of-plane angle of 90° and a light-source angle of 170°.

5. The method of claim 1, further comprising identifying a correct texture of the target coating.

6. The method of claim 1, wherein performing at least one of a visual evaluation and an instrument measurement includes visually determining a prominent color.

7. The method of claim 1, wherein determining one or more first colors includes calculating a similarity index.

8. A system for evaluating colorimetric and physical property attributes of cured complex coating mixtures, the system comprising:
a user interface; and
a processor in communication with the user interface and programmed to:
receive data from spectrophotometer measurement of a target coating on a target sample to generate colorimetric information;
identify a bulk toner that is present in the target coating, wherein identifying the bulk toner comprises:
receiving an in-plane spectrophotometer measurement of one or more first colors of the target coating at a single in-plane angle,
receiving an out-of-plane spectrophotometer measurement of one or more second colors of the target coating at a single out-of-plane angle, wherein the in-plane spectrophotometer measurement comprises different information than the out-of-plane spectrophotometer measurement,
comparing data from the in-plane spectrophotometer measurement and data from the out-of-plane spectrophotometer measurement to data within a database that comprises information for each bulk toner,
identify that the one or more first colors, which are measured from the single in-plane angle, are not within a particular tolerance of the one or more second colors, which are measured from the single out-of-plane angle, and
based upon the difference between the one or more first colors, which are measured from the single in-plane angle, and the one or more second colors, which are measured from the singe out-of-plane angle, determine that aluminum flake bulk toners or pearl bulk toners are present in the target coating based on a comparison of the single in-plane angle and single out-plane angle at specific angles;
identify at least one specific toner that is present in the target coating, wherein identifying the at least one specific toner comprises:
detecting a presence and an orientation of colored and/or non-colored pigmentation effects that are present in the target coating,
detecting a presence of colored and/or non-colored pigmentation effects that are present in the target coating; and
output a formulation of the target coating that includes at least the at least one specific toner.

9. The system of claim 8, wherein detecting a presence of colored and/or non-colored pigmentation effects that are present in the target coating comprises:
detecting a color of the target coating at a single viewing angle with a single light-source angle, wherein the single viewing angle and the single light-source angle are determined based upon the identified bulk toner, and
comparing the detected color to data within a database that comprises information for each specific toner.

10. The system of claim 8, further comprising a spectrophotometer in communication with the processor.

11. The system of claim 8, wherein the processor is programmed to identify the at least one specific toner by determining whether a colored aluminum and/or a pearl effect is present in the target coating.

12. The system of claim 8, wherein the processor is programmed to identify the at least one specific toner by identifying at least one of a solid effect and a non-colored aluminum.

13. An apparatus for evaluating colorimetric and physical property attributes of cured complex coating mixtures, the apparatus comprising:
means for receiving data from spectrophotometer measurement of a target coating on a target sample to generate colorimetric information; and
means for identifying a bulk toner that is present in the target coating, wherein identifying the bulk toner comprises:
detecting a presence and an orientation of colored and/or non-colored pigmentation effects that are present in the target coating,
receiving an in-plane spectrophotometer measurement of one or more first colors of the target coating at a single in-plane angle,
receiving an out-of-plane spectrophotometer measurement of one or more second colors of the target coating at a single out-of-plane angle, and
comparing data from the in-plane spectrophotometer measurement and data from the out-of-plane spectrophotometer measurement to data within a database that comprises information for each bulk toner,
identify that the one or more first colors, which are measured from the single in-plane angle, are not within a particular tolerance of the one or more second colors, which are measured from the single out-of-plane angle, and
based upon the difference between the one or more first colors, which are measured from the single in-plane angle, and the one or more second colors, which are measured from the single out-of-plane angle, determine that aluminum flake bulk toners or pearl bulk toners are present in the target coating based on a comparison of the single in-plane angle and single out-plane angle at specific angles;
output a formulation of the target coating that includes at least the at least one specific toner.

14. The apparatus of claim 13, further comprising means for identifying at least one specific toner including means for determining whether a colored aluminum and/or a pearl effect is present in the target coating.

15. The apparatus of claim 14, wherein the means for identifying the at least one specific toner includes means for identifying at least one of a solid effect and a non-colored aluminum.

16. A non-transitory computer readable medium including software for causing a processor to:
receive data from a spectrophotometer measurement of a target coating on a target sample to generate colorimetric information;
identify a bulk toner that is present in the target coating, wherein identifying the bulk toner comprises:
receiving a first in-plane spectrophotometer measurement of one or more first colors of the target coating at a single in-plane angle,
receiving a first out-of-plane spectrophotometer measurement of one or one or more second colors of the target coating at a single out-of-plane angle, wherein the first in-plane spectrophotometer measurement comprises different information than the first out-of-plane spectrophotometer measurement, and comparing data from the first in-plane spectrophotometer measurement and data from the first out-of-plane spectrophotometer measurement to data within a database that comprises information for each bulk toner;

identify at least one specific toner that is present in the target coating, wherein identifying the at least one specific toner comprises:

detecting a presence and an orientation of colored and/or non-colored pigmentation effects that are present in the target coating, receiving a second in-plane spectrophotometer measurement of one or more third colors of the target coating at a single in-plane angle, receiving a second out-of-plane spectrophotometer measurement of one or one or more fourth colors of the target coating at a single out-of-plane angle, wherein the second in-plane spectrophotometer measurement comprises different information than the second out-of-plane spectrophotometer measurement, compare data from the second in-plane spectrophotometer measurement and data from the second out-of-plane spectrophotometer measurement to data within the database that comprises information for each specific toner, identify that the one or more first colors, which are measured from the single in-plane angle, are not within a particular tolerance of the one or more second colors, which are measured from the single out-of-plane angle, and based upon the difference between the one or more first colors, which are measured from the single in-plane angle, and the one or more second colors, which are measured from the single out-of-plane angle, determine that aluminum flake bulk toners or pearl bulk toners are present in the target coating based on a comparison of the single in-plane angle and single out-plane angle at specific angles; and output a formulation of the target coating that includes at least the at least one specific toner.

* * * * *